(12) United States Patent
Propst et al.

(10) Patent No.: US 7,582,154 B2
(45) Date of Patent: Sep. 1, 2009

(54) COMPOSITIONS OF POLYOL GRANULES AND PROCESSES OF MANUFACTURE

(75) Inventors: Cecil W. Propst, Norton Shores, MI (US); Ronald C. Deis, East Goshen, PA (US)

(73) Assignee: Corn Products International, Inc., Westchester, IL (US)

( * ) Notice: Subject to any disclaimer, the term of this patent is extended or adjusted under 35 U.S.C. 154(b) by 452 days.

(21) Appl. No.: 11/191,792

(22) Filed: Jul. 28, 2005

(65) Prior Publication Data
US 2006/0078663 A1 Apr. 13, 2006

Related U.S. Application Data

(63) Continuation of application No. PCT/US2004/002744, filed on Jan. 29, 2004.

(60) Provisional application No. 60/443,719, filed on Jan. 29, 2003.

(51) Int. Cl.
*C08L 5/00* (2006.01)
*C08B 37/00* (2006.01)
*C08B 30/18* (2006.01)
*A23G 3/42* (2006.01)

(52) U.S. Cl. .................. 106/217.7; 426/658; 536/103; 536/123.13; 536/124

(58) Field of Classification Search ................ 426/658; 106/162.1, 217.7; 536/1.11, 103, 123.12, 536/124
See application file for complete search history.

(56) References Cited

U.S. PATENT DOCUMENTS

| | | | | |
|---|---|---|---|---|
| 4,789,559 A | * | 12/1988 | Hirao et al. ................. | 426/658 |
| 5,120,550 A | * | 6/1992 | Van der Schueren .......... | 426/3 |
| 5,304,388 A | * | 4/1994 | Ueno et al. ................. | 426/658 |
| 5,616,361 A | * | 4/1997 | Virtanen et al. ............. | 426/658 |
| 6,458,401 B1 | | 10/2002 | Beauregard et al. | |

OTHER PUBLICATIONS

PCT/US04/02744 International Search Report dated Oct. 6, 2004.

* cited by examiner

*Primary Examiner*—David M Brunsman
(74) *Attorney, Agent, or Firm*—Foley & Lardner LLP

(57) ABSTRACT

The present invention includes methods for preparing polyol products including a method of making a free-flowing granular product comprising: a) charging hydrogenated starch hydrolysate to an agglomerator; b) adding polyol syrup to the maximum loading capacity of the hydrogenated starch hydrolysate; and c) adding polyol crystals in an amount sufficient to dry the product. The present invention also includes compositions comprising polyol products for use in pharmaceuticals, nutraceuticals, foods, such as frozen dairy and bakery items, and confections.

9 Claims, 1 Drawing Sheet

| | ERYTHRITOL | XYLITOL | MANNITOL | SORBITOL | MALTITOL | ISOLMALT | LACTITOL | SUCROSE |
|---|---|---|---|---|---|---|---|---|
| NO. OF CARBONS | 4 | 5 | 6 | 6 | 12 | 12 | 12 | 12 |
| MOLECULAR WEIGHT | 122 | 152 | 182 | 182 | 344 | 344 | 344 | 342 |
| MELTING POINT (°CELSIUS) | 121 | 94 | 165 | 97 | 150 | 145-150 | 122 | 190 |
| GLASS TRANSITION TEMPERATURE (°CELSIUS) | -42 | -33 | -39 | -5 | 47 | 34 | 33 | 52 |
| HEAT OF SOLUTION (KCAL/KG) | -43 | -36.5 | -28.5 | -26 | -18.9 | -9.4 | -13.9 | -4.3 |
| HEAT STABILITY (°CELSIUS) | >160 | >160 | >160 | >160 | >160 | >160 | >160 | <150 |
| ACID STABILITY pH | 2-10 | 2-10 | 2-10 | 2-10 | 2-10 | 2-10 | >3 | Hydrolyses |
| SOLUBILITY WW% (25 °C) | 36 | 66 | 18 | 72 | 60 | 28 | 58 | 67 |
| HYGROSCOPICITY | VERY LOW | LOW | VERY LOW | HIGH | LOW | LOW | MEDIUM | MEDIUM |

|  | ERYTHRITOL | XYLITOL | MANNITOL | SORBITOL | MALTITOL | ISOLMALT | LACTITOL | SUCROSE |
|---|---|---|---|---|---|---|---|---|
| NO. OF CARBONS | 4 | 5 | 6 | 6 | 12 | 12 | 12 | 12 |
| MOLECULAR WEIGHT | 122 | 152 | 182 | 182 | 344 | 344 | 344 | 342 |
| MELTING POINT (°CELSIUS) | 121 | 94 | 165 | 97 | 150 | 145-150 | 122 | 190 |
| GLASS TRANSITION TEMPERATURE (°CELSIUS) | -42 | -33 | -39 | -5 | 47 | 34 | 33 | 52 |
| HEAT OF SOLUTION (KCAL/KG) | -43 | -36.5 | -28.5 | -26 | -18.9 | -9.4 | -13.9 | -4.3 |
| HEAT STABILITY (°CELSIUS) | >160 | >160 | >160 | >160 | >160 | >160 | >160 | <150 |
| ACID STABILITY pH | 2-10 | 2-10 | 2-10 | 2-10 | 2-10 | 2-10 | >3 | Hydrolyses |
| SOLUBILITY WW% (25 °C) | 36 | 66 | 18 | 72 | 60 | 28 | 58 | 67 |
| HYGROSCOPICITY | VERY LOW | LOW | VERY LOW | HIGH | LOW | LOW | MEDIUM | MEDIUM |

FIG. 1

COMPOSITIONS OF POLYOL GRANULES AND PROCESSES OF MANUFACTURE

STATEMENT OF RELATED APPLICATIONS

This application is a continuation of co-pending International PCT Application No. PCT/US2004/002744 filed on Jan. 29, 2004, which claims priority to U.S. Provisional Application No. 60/443,719, filed on Jan. 29, 2003 both of which are hereby incorporated by reference in their entirety.

FIELD OF THE INVENTION

The present invention relates to a process for forming a free-flowing granular polyol product. The present invention also relates to granular polyol products for use in preparing sugar-free pharmaceuticals, nutraceuticals, foods, such as frozen dairy and bakery items, and confections.

BACKGROUND OF THE INVENTION

Current processes for producing maltitol crystals from maltitol syrup use high temperatures and thin films to dehydrate a syrup, thereby converting the syrup to a solid form. The high viscosity, tackiness, and rubbery nature of maltitol syrup as it dries creates the need for high energy machinery and thin film evaporators, both of which use high temperatures to transition the syrup from a wet syrup to a dry granule.

For example, the film deposition method for producing maltitol crystals from maltitol syrup places a layer of syrup on the surface of a steam heated cylinder. The syrup is dried into a film that is thin enough to maintain motion during the rubbery transitional phase and to maintain reasonable evaporation rates. A similar technology uses high barrel temperatures and high torque to extrude malitol syrup into a mixture with maltitol crystals and dries by tray drying.

BRIEF DESCRIPTION OF THE DRAWINGS

FIG. 1 is a table listing the physical properties of maltitol and other polyols and/or sugars.

BRIEF SUMMARY OF THE INVENTION

In one embodiment, a process for preparing a granular polyol (e.g., maltitol) product is described. In one embodiment, a polyol (e.g., maltitol) syrup is distributed onto crystals of the polyol (e.g., maltitol crystals) and the combined composition is dried. In one embodiment, the dried composition is milled to a desired particle size with conventional size-reduction machinery, for example, a FITZMILL™ (Fitzpatrick D-6 Mill, Elmhurst, Ill.). In one embodiment, the dried combined composition is size-screened to a desired particle size with conventional sieves, for example, a vibratory sieve (Sweco, Florence, Ky.) to form a customized sweetener ("customized sweetener 1"). In another embodiment, hydrogenated starch hydrolysate (HSH) powder is added to customized sweetener 1, and optionally dried again to form a free flowing granular maltitol product ("customized sweetener 2").

In one embodiment, the polyol syrup and the polyol crystals of the present invention are different polyols.

In one embodiment, the polyol syrup includes more than one polyol, and the polyol crystals include more than one polyol.

In yet another embodiment, crystalline maltitol, customized sweetener 1, customized sweetener 2, and/or mixtures thereof, are combined with other ingredients, such as fats, oils, cocoa, and/or milk solids, to produce a sugar-free coating for use in preparing and/or coating sugar-free foods, confections, nutraceuticals, and pharmaceuticals.

In another embodiment of the present invention, crystalline maltitol, customized sweetener 1, customized sweetener 2, and/or mixtures thereof, are processed so that the particle size distribution is narrow, and the level of fines (particles smaller than a 100 mesh sieve) produced is decreased. Products according to the present invention of a particle size of from about 200 to about 2000 microns are prepared using this screening and milling process.

In another embodiment of the method of the present invention, a polyol (e.g., maltitol) syrup and hydrogenated starch hydrolysate (HSH) are agglomerated. Maltitol crystals are added to dry out the product. The resulting composition is then pressed through an extruder and dried to obtain a free flowing granular product, according to one aspect of the present invention.

In another embodiment of the present invention, a method includes a free-flowing granular product. The method includes charging solid HSH to an agglomerator, adding polyol syrup to the maximum loading capacity of the hydrogentated starch hydrolysate; and adding polyol crystals in an amount sufficient to dry the product. In an embodiment of the invention, the method also includes separating a predetermined particle size from the granular composition.

The present invention also includes polyol products that include granular maltitol. In one embodiment, the composition also includes granular maltitol and HSH.

The present invention eliminates the need for high temperatures and creation of polyol syrup (e.g., maltitol syrup) films, and serves as an inexpensive method for drying polyol syrup into polyol (e.g., maltitol) crystals, granules, and agglomerates.

DETAILED DESCRIPTION

The present invention relates to granular polyol compositions and methods for their manufacture.

Definitions

As used herein, the term "about" will be understood by persons of ordinary skill in the art and will vary to some extent on the context in which it is used. If there are uses of the term which are not clear to persons of ordinary skill in the art given the context in which it is used, "about" shall mean up to plus or minus 10% of the particular value.

By the term "granular" is meant discrete particles, grains, or granules. In one embodiment, the granular polyols have a high density and a low porosity. In one embodiment, the granular polyols have a spherical or polyhedric shape.

Description

In one embodiment, the present invention includes compositions including polyol granules, (e.g., maltitol granules), and methods for preparing polyol granules. Polyols useful in the present invention include, but are not limited to syrup and crystals of maltitol, erythritol, xylitol, mannitol, sorbitol, isomalt, lactitol, and mixtures thereof. The compositions of the present invention are useful in preparing sugar-free compositions for use in, for example, pharmaceuticals, nutraceuticals, foods, and/or confections.

For all of the embodiments discussed herein, a polyol syrup can be any polyol syrup. In one embodiment, the polyol syrup is maltitol syrup, for example, MALTISWEET™ M95 (SPI Polyols, Inc., New Castle, Del.) or MALTISWEET™ MH80 (SPI Polyols, Inc., New Castle, Del.). MALTISWEET™ M95 is about 90% as sweet as sucrose and has a polyol distribution of about 2% sorbitol by weight, 90% maltitol by weight, and about 8% of a polyol consisting of a hydrogenated polymer with three or more glucose units. MALTISWEET M95™ contains about 33-35% moisture by weight, a maximum of 0.1% ash, and about 0.3% reducing sugar. A 20% solution of MALTISWEET M95™ has a pH of about 5.0-8.0. MALTISWEET M95™ is useful in confectionery, bakery, frozen dairy, and other foods.

MALTISWEET™ MH80 provides the sweetness and stability of hard sugar candy, and has a polyol distribution of no more than about 2% sorbitol by weight and no less than about 72% maltitol by weight. Other general characteristics of MALTISWEET™ MH80 can be found in Table 1.

TABLE 1

General Characteristics of MALTISWEET ™ MH80

| | |
|---|---|
| Form of the solution at 25° C. | clear, viscous liquid |
| Viscosity at 25° C. | 2300 cps |
| Flash Point | above 150° C. |
| Boiling Point at 760 mmHg | approximately 105° C. |
| Specific Gravity | Approximately 1.36 |
| Water | Approximately 25% |
| Polyol distribution (HP 1 is a hydrogenated polymer with one glucose unit; HP 2 has two glucose units; HP 3 has three or more glucose units) | HP 1 (sorbitol) <2% HP 2 (maltitol) >72% HP 3 and above >20% |
| Reducing Sugars | 0.3% maximum |
| Residue on ignition | 0.1% maximum |
| Chlorides, ppm | 50 maximum |
| Sulfates, ppm | 100 maximum |
| Lead, ppm | 1 maximum |
| Heavy metals, ppm | 10 maximum |

Other polyol syrups useful in the present invention include MALTISWEET™ 3145 (SPI Polyols, Inc. New Castle, Del.), MALTISWEET™ IC (SPI Polyols, Inc. New Castle, Del.), MALTISWEET™ MH65 (SPI Polyols, Inc. New Castle, Del.), and MALTISWEET™ B (SPI Polyols, Inc. New Castle, Del.).

Other polyol syrups, such as, for example, SORBO X45™ (SPI Polyols, Inc., New Castle, Del.), which is a combination of xylitol and sorbitol, and combinations thereof are also useful in the present invention.

The HSH powder can be, for example STABILITE™ SD30 or SD60 (INNOVA, Muscatine, Iowa). The polyol distribution for STABILITE™ SD30 is about 2% sorbitol by weight and about 6% maltitol by weight and the polyol distribution for STABILITE™ SD60 is about 1% sorbitol and about 3.5% maltitol. Other general characteristics of the STABILITE™ family of products is listed in Table 2.

TABLE 2

General Characteristics of the STABILITE ™ Products

| | STABILITE SD30 | STABILITE SD60 |
|---|---|---|
| Moisture | 8% maximum | 8% maximum |
| Ash | 0.1% maximum | 0.1% maximum |
| pH of 20% solution | 4.0-5.0 | 4.0-5.0 |
| Reducing Sugars | 1.0% maximum | 1.0% maximum |
| Viscosity of 50% solution at 25° C. | about 90 cP | about 280 cP |
| Osmolality of 20% solution | About 278 mOsm | About 185 mOsm |
| Polyol distribution | HP 1 (sorbitol) ~2% HP 2 (maltitol) ~6% HP 3 and above ~92% | HP 1 (sorbitol) ~1% HP 2 (maltitol) ~3.5% HP 3 and above ~95.5% |

In one embodiment, HSH powder is a mixed polyol composition where no one polyol is present in a quantity greater than 50% by weight. The HSH powder serves to add bulk to the resulting polyol granule composition, but because of its neutrality, it typically does not affect the sweet taste provided by the polyol (e.g., maltitol) syrup, and does not impart a cooling effect like all other polyols. In addition, HSH powder has a decreased laxation effect (i.e., a high laxation threshold), which allows for increased consumption before there is a laxative effect is produced, e.g., over 150 grams per day.

In one embodiment, the polyol crystals can be any polyol crystal material. In one embodiment, the polyol crystals are maltitol crystals, for example, an AMALTY® product (Towa Chemical Industry Co., Ltd., Tokyo, JAPAN). AMALTY® crystals are about 90% as sweet as sucrose, and the product is available in three varieties, depending on the size of the crystal: AMALTY® MRS, AMALTY® MR20, AMALTY® MR50, and AMALTY® MR100, which are useful in the present invention. One hundred percent of the MR20 crystals pass through a #20 U.S. sieve. A minimum of 95% of the MR50 crystals pass through a #48 U.S. sieve and a maximum of 65% of the MR50 crystals pass through a #200 U.S. sieve. A minimum of 80% of the MR100 crystals pass through a #250 U.S. sieve. General characteristics of the AMALTY family of products are listed in Table 3.

TABLE 3

General Characteristics of AMALTY Products

| | |
|---|---|
| Form of the solution at 25° C. | white, crystalline powder |
| Hygroscopicity | nonhygroscopic |
| Assay, % anhydrous basis | 92.5 minimum |
| Water | Approximately 1.5% |
| Arsenic, ppm | 2.5 maximum |
| Reducing Sugars | 0.3% maximum |
| Residue on ignition | 0.1% maximum |
| Chlorides | 0.005% maximum |
| Sulfates | 0.01% maximum |
| Lead, ppm | 1 maximum |
| Heavy metals, ppm | 10 maximum |
| Taste | 90% as sweet as sucrose |

Other sources of maltitol crystals include MALTISORB™ (Roquette, FRANCE).

Generally, the method of the present invention includes combining polyol crystals, (e.g., maltitol crystals), a polyol syrup (e.g., maltitol), and optionally, HSH, drying the mixture, and processing the mixture to a relatively uniform particle size, preferably within a range of between about 200 and 2000 microns. The drying step can be performed using conventional drying machinery, such as a fluid bed granulator, for example, a Fluid Air Model 50 dryer (Fluid Air, Aurora, Ill.). The drying temperature can be in the range of 45 to 120 degrees Celsius, and is preferably between 70 to 90 degrees Celsius. The air velocity on the fluid bed dryer can be in the range of 100 to 300 standard cubic feet per minute (scfm), and preferably is in the range of 150 to 250 scfm.

The particle size depends to some extent upon the amount of water present in the composition. Typically, a higher water content produces larger particle sizes. Ultimately, a free flowing granular polyol (e.g., maltitol) product is formed that is useful in preparing sugar-free compositions for use in the food and confectionery industry, as well as for use in the pharmaceutical and nutraceutical industries. The resulting polyol granule approximates the hygroscopicity and free flowability of the AMALTY® maltitol crystal family of products.

In one embodiment of the method of the present invention, granules of polyols (e.g., maltitol) are generated from polyol syrup (e.g., maltitol syrup) by pouring or spraying (using conventional spraying techniques, such as spray drying) the syrup onto a bed of polyol crystals (e.g., maltitol crystals). In one embodiment, the polyol syrup (e.g., maltitol syrup) includes at least about 50% by weight polyol solids, and preferably includes from about 50% to about 70% polyol solids.

Preferably, about 5% to about 80% by weight, of polyol (e.g., maltitol) syrup is distributed, for example, by pouring or by spraying using conventional spraying techniques, to the polyol crystals (e.g., maltitol crystals). More preferably, about 10% to about 70% of polyol (e.g., maltitol) syrup, more preferably about 20% to about 60%, more preferably about 30% to about 50% by weight, polyol (e.g., maltitol) syrup is distributed to the polyol crystals (e.g., maltitol crystals), and thereby forms a crystal/syrup composition, according to one aspect of the present invention.

In a preferred embodiment of the present invention, the percent ratio by weight of polyol (e.g., maltitol) syrup to polyol crystals (e.g., maltitol crystals)about 5:95 to about 30:70. In one embodiment, the ratio is about 5:95, respectively, more preferably from about 10:90, more preferably from about 20:80, and more preferably from about 30:70, respectively.

In one embodiment, the combination of polyol syrup and polyol crystals is partially dried using a fluid bed dryer (Fluid Air, Model 50, Aurora Ill.) such that the water content is from about 1% to about 7% by weight. The drying temperature can be in the range of about 45 to about 120 degrees Celsius, and is preferably between about 70 to about 90 degrees Celsius. The air velocity on the fluid bed dryer can be in the range of about 100 to about 300 standard cubic feet per minute (scfm), and preferably is in the range of about 150 to about 250 scfm.

Preferably, the water content is from about 1% to about 5%, and more preferably, from about 1% to about 3% for the reasons described herein. To obtain larger polyol (e.g., maltitol) particles, the water content is most preferably about 3% or higher. To obtain smaller particles, the water content is preferably about 1%. After drying to a desired water content (i.e., 1% to 7% water), "customized sweetener 1" is produced. The resultant customized sweetener 1 is optionally sized by passing the sweetener through an appropriately sized mesh or screen. Sizing and/or screening may be performed, for example, using a vibratory sieve (Sweco, Florence, Ky.). In an embodiment of the invention, the mesh size of the sieve is from about 10 to about 100 (corresponding to about 2000 to 150 microns). In another embodiment, the mesh size is from about 20 to about 60 mesh (850 to 250 microns). In another embodiment, the mesh size is about 30 to about 50 mesh (600 to 300 microns).

In another embodiment of the present invention, HSH is added to customized sweetener 1 to form a free flowing granular product that preferably has increased particle surface integrity, and enhanced particle separation.

In one embodiment of the method of the present invention, about 5% to about 50% by weight HSH powder, by weight, is added to customized sweetener 1. Preferably, about 10% to about 40% HSH, by weight, is added, and more preferably, about 15% to about 30% HSH is added to customized sweetener 1 to further dry the product. The resulting product, "customized sweetener 2," can be used as is.

Alternatively, in another embodiment of the method of the present invention, customized sweetener 2 can be further dried to less than about 2% moisture by weight using a fluid-bed dryer to produce a product with increased flowability, relative to the non-dried composition containing HSH. The target moisture content is preferably from about 0.5% to about 3%, and more preferably from about 0.5% to about 1.5%. In an embodiment where the water content of customized sweetener 1 is about 3% or greater, addition of HSH results in granules having a larger particle size, i.e., larger than 100 mesh. In an embodiment where the water content of customized sweetener 1 is less than about 3%, preferably about 0.5% to about 1.5%, addition of HSH powder results in granules having a smaller particle size, preferably around 150 microns.

Products according to the present invention can have particle sizes from about 50 microns to about 2000 microns. In one embodiment, the particle size is about 50 microns to about 850 microns. In one embodiment, the particle size is about 50 microns to about 600 microns. In one embodiment, the particle size is about 50 microns to about 300 microns. In one embodiment, the particle size is about 50 microns to about 250 microns. In one embodiment, the particle size is about 70 to about 80 microns.

In another embodiment of the method of the present invention, HSH is charged to an agglomerator (Peerless Sigma Mixer, DA 100, Sidney, Ohio), and polyol (e.g., maltitol) syrup is added to the maximum loading capacity of the HSH. The resulting product has a pasty or sandy consistency and has a water content of about 25%. Crystalline polyol (e.g., maltitol, such as AMALTY™, AMALTY™ MRS, AMALTY™ MR20, AMALTY™ MR50, or AMALTY™ MR100 (Towa Chemical Industry Co., Ltd., Tokyo, JAPAN)) is added in sufficient amount to dry out the product. The particles are screened to the desired size. In one embodiment, the particle size ranges from about 50 to about 2000 microns. In another embodiment of the invention, the particle size ranges from about 50 to about 850 microns. In another embodiment of the invention, the particle size ranges from about 50 to about 600 microns. In another embodiment of the invention, the particle size ranges from about 50 to about 300 microns. In another embodiment of the invention, the particle size ranges from about 50 to about 250 microns. In another embodiment of the invention, the particle size ranges from about 70 to about 80 microns.

To the extent that the product is too wet, and therefore too agglomerated, the product is pressed through an extruder, such as a Reitz RE-6 model extruder (Hosokawa Bepex, Minneapolis, Minn.) to form an extrudate and the extrudate is dried to less than 2% moisture content in a fluid bed dryer, such as a Fluid Air Model 1000 (FluidAir, Aurora, Ill.) to produce a granular free flowing product. The resulting product can also be used in any of the product embodiments discussed herein.

In another embodiment of the present invention, either crystalline polyol (e.g., maltitol), customized sweetener 1, customized sweetener 2, or combinations thereof are used to prepare a sugar-free "premix" product. The sweetener or combination of sweeteners is combined with other components of sugar free coatings, such as, for example, vegetable fats, milk solids, and cocoa, in a blender and pressed through, for example, a roll refiner or a jet mill to reduce the particle size to a predetermined particle size (and thereby increase uniformity of the particle size) of the product. In an embodiment of the invention, the particle size is less than about 30 microns. Accordingly, products of the present invention can be used to form a sugar-free coating.

In another embodiment of the invention, the particle size is from about 10 to about 20 microns. In another embodiment of the invention, the particle size is from about 10 to about 2000 microns in size.

The resulting products of the methods of the present invention are particularly useful in manufacturing plants where both sugar and sugar-free products are produced. Usually, the same machinery (e.g., blender and roll refiner) is used to produce both the sugar and sugar-free products, and there is a strong probability of contaminating the sugar-free product with sugar because it is difficult to completely remove the sugar from the machinery. The products of the present invention can be introduced later in the manufacturing process during the conching step (the texture-smoothing step) as opposed to earlier in the process where contact with the blender and the roll refiner may cause sugar contamination. The compositions of the present invention therefore serve to reduce and/or eliminate contamination of sugar-free products with sugar.

As noted above, in some embodiments of the present invention, crystalline polyol, (e.g., maltitol), customized sweetener 1, customized sweetener 2, and/or combinations thereof are produced such that the compositions have a larger predetermined particle size for use in preparing products such as sugar-free chocolate, where high fines output is problematic as described below and low fines output is desirable. Also, the range of particle size is narrow to enhance a low fines output. In one embodiment, the particles collected pass through a 100 mesh screen. In another embodiment, the particles collected fall between a 100 mesh screen and a 325 mesh screen. In another embodiment, the particles collected pass through a 325 mesh screen.

High fines output is problematic because excess fines absorb a higher amount of fat, which is an expensive ingredient for food, bakery, frozen dairy, and confectionery manufacturers. Currently, the most common type of crystalline maltitol has a high level of fines (i.e., particles that pass through a 100 mesh sieve). Thus, a crystalline maltitol having less fines absorbs less fat, and makes it less expensive for a manufacturer to produce the same product.

EXAMPLE

About 550 grams of MALTISWEET 3145 syrup maltitol was cooked at about 127° Celsius to obtain about 90% solids. About 240 grams of the cooked MALTISWEET™ 3145 product was combined with about 500 grams of AMALTY™ MRS crystalline maltitol and mixed in a Hobart mixer with a Delta paddle (Hobart, Troy, Ohio) on speed one until uniform. The product formed popcorn-sized pieces, which were dried overnight in a controlled environment oven (Hotpack, Phila., Pa.) at about 40° Celsius and 10% relative humidity. The resulting product can be milled and sized to a desired particle size in accordance with the present invention.

One or more features, aspects, or embodiments of the present invention can be combined with one or more other features, aspects or embodiments of the present invention.

It will be apparent to those skilled in the art that various modifications and variations can be made in the methods and compositions of the present invention without departing from the spirit or scope of the invention. Thus, it is intended that the present invention cover the modifications and variations of the present invention provided they come within the scope of the appended claims and their equivalents.

What is claimed is:

1. A method of making a free-flowing granular product comprising:
   a) charging hydrogenated starch hydrolysate to an agglomerator;
   b) adding polyol syrup to the maximum loading capacity of the hydrogenated starch hydrolysate; and
   c) adding polyol crystals in an amount sufficient to dry the product.

2. The method of claim 1, wherein the polyol syrup is maltitol and the polyol crystal is maltitol.

3. The method of claim 1, further comprising separating a desired particle size from the granular composition.

4. The method of claim 3, wherein said particle size is from about 50 to about 2000 microns.

5. The method of claim 3, wherein said particle size is from about 50 to about 850 microns.

6. The method of claim 3, further comprising pressing the product through an extruder to form an extrudate.

7. The method of claim 6, wherein the extrudate has a moisture content of less than about 2 percent.

8. The method of claim 1, wherein the polyol syrup and the polyol crystals are different polyols.

9. The method of claim 1, wherein the polyol syrup and polyol crystals are selected from the group consisting of: maltitol, erythritol, xylitol, mannitol, sorbitol, isomalt, lactitol, and mixtures thereof.

* * * * *